US012097098B2

(12) United States Patent
Axborn et al.

(10) Patent No.: US 12,097,098 B2
(45) Date of Patent: Sep. 24, 2024

(54) ABSORBENT ARTICLE

(71) Applicant: Essity Hygiene and Health Aktiebolag, Gothenburg (SE)

(72) Inventors: Peter Axborn, Gothenburg (SE); Helena Corneliusson, Gothenburg (SE)

(73) Assignee: ESSITY HYGIENE AND HEALTH AKITEBOLAG, Gothenburg (SE)

( * ) Notice: Subject to any disclaimer, the term of this patent is extended or adjusted under 35 U.S.C. 154(b) by 533 days.

(21) Appl. No.: 17/621,345

(22) PCT Filed: Jul. 7, 2020

(86) PCT No.: PCT/SE2020/050713
§ 371 (c)(1),
(2) Date: Dec. 21, 2021

(87) PCT Pub. No.: WO2021/015656
PCT Pub. Date: Jan. 28, 2021

(65) Prior Publication Data
US 2022/0362065 A1    Nov. 17, 2022

(30) Foreign Application Priority Data

Jul. 19, 2019 (WO) .................. PCT/SE2019/050704
Jul. 19, 2019 (WO) .................. PCT/SE2019/050705
Jul. 19, 2019 (WO) .................. PCT/SE2019/050706

(51) Int. Cl.
*A61F 13/532* (2006.01)
*A61F 13/15* (2006.01)
(Continued)

(52) U.S. Cl.
CPC ........ *A61F 13/15203* (2013.01); *A61F 13/49* (2013.01); *A61F 13/53* (2013.01);
(Continued)

(58) Field of Classification Search
CPC ...... A61F 13/53; A61F 13/532; A61F 13/533; A61F 13/535; A61F 13/536;
(Continued)

(56) References Cited

U.S. PATENT DOCUMENTS 3,769,978 A * 11/1973 DeNight ................ A61F 13/533
 604/397
6,099,515 A *  8/2000 Sugito .................... A61F 13/536
 604/385.01
(Continued)

FOREIGN PATENT DOCUMENTS

EP  0525778 A2  2/1993
EP  1000597 A2  5/2000
(Continued)

OTHER PUBLICATIONS

International Preliminary Report on Patentability and Written Opinion of the International Searching Authority (Forms PCT/IB/373 and PCT/ISA/237) issued on Jan. 25, 2022, by the International Bureau of WIPO, in corresponding International Application No. PCT/SE2020/050713. (9 pages).
(Continued)

*Primary Examiner* — Catharine L Anderson
(74) *Attorney, Agent, or Firm* — Buchanan Ingersoll & Rooney PC

(57) ABSTRACT

An absorbent article includes an absorbent core. The absorbent core includes an absorbent component enclosed by a core cover. The absorbent component includes a coherent area having an extension of the absorbent article and having an extension in the transverse direction over a full width of the absorbent component, the coherent area having a front edge and a back edge. The absorbent component includes high density areas of absorbent material alternating with low density areas of absorbent material. The high density areas and the low density areas extending in the longitudinal
(Continued)

direction of the absorbent article in the front portion and/or in the crotch portion of the absorbent article. The back portion of the absorbent article includes a conformance zone comprising absorbent material. The coherent area and the conformance zone are separated by an area substantially free from absorbent material.

24 Claims, 5 Drawing Sheets

(51) Int. Cl.
*A61F 13/49* (2006.01)
*A61F 13/53* (2006.01)
*A61F 13/533* (2006.01)
*A61F 13/535* (2006.01)
*A61F 13/536* (2006.01)

(52) U.S. Cl.
CPC .......... *A61F 13/532* (2013.01); *A61F 13/533* (2013.01); *A61F 13/535* (2013.01); *A61F 13/536* (2013.01); *A61F 2013/15406* (2013.01); *A61F 2013/1543* (2013.01); *A61F 2013/49084* (2013.01); *A61F 2013/5307* (2013.01)

(58) Field of Classification Search
CPC .. A61F 2013/15406; A61F 2013/15422; A61F 2013/1543; A61F 2013/49084; A61F 2013/5326
See application file for complete search history.

(56) References Cited

U.S. PATENT DOCUMENTS

| | | | |
|---|---|---|---|
| 6,703,330 | B1 | 3/2004 | Marsh |
| 7,547,815 | B2* | 6/2009 | Ohashi ................. A61F 13/536 604/385.01 |
| 8,604,270 | B2 | 12/2013 | Venturino et al. |
| 10,596,044 | B2* | 3/2020 | Umemoto ........... B29C 65/4815 |
| 2003/0120235 | A1* | 6/2003 | Boulanger .......... A61F 13/4758 604/385.01 |
| 2013/0245588 | A1* | 9/2013 | Mishima ............... A61F 13/496 604/374 |
| 2015/0342796 | A1 | 12/2015 | Bianchi et al. |
| 2017/0312137 | A1 | 11/2017 | Degrave et al. |

FOREIGN PATENT DOCUMENTS

| | | |
|---|---|---|
| EP | 1920743 A2 | 5/2008 |
| EP | 2949302 A1 | 12/2015 |
| EP | 3329890 A1 | 6/2018 |
| JP | 2019097898 A | 6/2019 |
| JP | 2019103789 A | 6/2019 |

OTHER PUBLICATIONS

International Search Report (PCT/ISA/210) and Written Opinion (PCT/ISA/237) mailed on Sep. 9, 2020, by the Swedish Patent Office as the International Searching Authority for International Application No. PCT/SE2020/050713.

* cited by examiner

ABSORBENT ARTICLE

TECHNICAL FIELD

The disclosure pertains to an absorbent article comprising an absorbent core which is sandwiched between a liquid-permeable topsheet and a liquid-impermeable backsheet. The absorbent core comprises an absorbent component which is enclosed by a core cover.

BACKGROUND

In the field of disposable absorbent articles, such as disposable absorbent diapers and pant-type articles, there is a general desire to provide the absorbent articles with a snug and body conforming fit as well as absorbency and leakage security. In addition, there is a continuing need for improvements in particular with regard to reduction of material consumption as well as cost efficiency when manufacturing disposable absorbent articles. There is also an increasing concern that the amount of material used in disposable absorbent articles is kept to a minimum from an environmental point of view. Hence, there is a desire for disposable absorbent articles which require less raw material, with the location of absorbent material in the article tailored towards the user's anatomy and needs.

U.S. Pat. No. 8,604,270 discloses an absorbent core comprising an elongate liquid holding formation and an outer region of fibrous material located outward of the liquid holding formation.

SUMMARY

The present disclosure is based on the insight that an absorbent article having improved fit and body conformance as well as good functionality with regard to absorbency, liquid distribution properties and leakage security, may be achieved by a combination of selected features in an absorbent core of the article.

The absorbent articles referred to herein are wearable and disposable absorbent articles, for example in the form of open diapers, pant diapers, belted diapers, incontinence garments, feminine hygiene garments and the like, as well as absorbent inserts which are worn inside a support garment, such as a support pant or ordinary underwear. The articles are used to absorb, distribute and store various types of body exudates while providing a high level of comfort and a sense of dryness to the wearer during use.

Disposable absorbent articles having good functionality, fit and body conformance may be achieved. Variations of the disclosure are set out in the dependent claims.

Disclosed herein is an absorbent article comprising an absorbent core sandwiched between a liquid-permeable topsheet and a liquid-impermeable backsheet, the article having a longitudinal direction along a central longitudinal axis and a transverse direction along a central transverse axis extending perpendicular to the longitudinal axis. The absorbent article having a front end edge extending in the transverse direction and a back end edge extending in the transverse direction and a first side edge extending in the longitudinal direction and a second side edge extending in the longitudinal direction. The absorbent article comprising a front portion, a back portion and a crotch portion located between the front portion and the back portion. The absorbent core comprises an absorbent component, the absorbent component being enclosed by a core cover. The absorbent component comprising a coherent area, the coherent area having an extension in the longitudinal direction in at least the front portion and the crotch portion of the absorbent article and having an extension in the transverse direction over a full width of the absorbent component inside the core cover, the coherent area having a front edge and a back edge. The absorbent component comprises high density areas of absorbent material alternating with low density areas of absorbent material. The high density areas of absorbent material and the low density areas of absorbent material extending in the longitudinal direction of the absorbent article in the front portion and/or in the crotch portion of the absorbent article. The back portion of the absorbent article comprises a conformance zone comprising absorbent material. The coherent area and the conformance zone are separated vertically by an area substantially free from absorbent material.

The area separating, i.e. the area located between, the coherent area and the conformance zone provides flexure to the absorbent structure. The area separating the coherent area and the conformance zone may traverse the whole width of the absorbent component. The area is substantially free from absorbent material and may have a basis weight of less than 50 gsm, such as less than 25 gsm, such as less than 5 gsm. The area separating the coherent area and the conformance zone may have a width of 2-30 mm, such as 2-20 mm, such as 5-10 mm.

The absorbent material in the conformance zone may be arranged to enhance the beneficial properties of the area separating the coherent area and the conformance zone and may comprise any of, or a combination of, the following: The conformance zone may not comprise areas being free from absorbent material. The absorbent material in the conformance zone may not comprise individual clusters of absorbent material having a diameter larger than 10 mm. The distribution of absorbent material in the conformance zone may be uniform or substantially uniform. The density of the absorbent material in the conformance zone may be substantially uniform. The conformance zone may comprise a homogenous, or substantially homogenous mixture of superabsorbent material and cellulose fibers. The mixture of superabsorbents and cellulosic fibers in the conformance zone may have a basis weight coefficient of variation of at most 20%, as measured according to the method for measuring basis weight evenness provided in this disclosure.

The conformance zone may be symmetrically orientated in relation to the longitudinal axis and wherein the conformance zone has a triangular shape, a D shape, a W shape, a square or a rectangular shape.

The absorbent material in the conformance zone may have a lower density than the absorbent material in the high density areas in the coherent area.

The absorbent material in the conformance zone may have a lower basis weight than the absorbent material in the high density areas in the coherent area.

The ratio of basis weight of the absorbent material in the conformance zone to the basis weight in the high density areas may be from 1.5 to 4.

The ratio of the density of the absorbent material in the conformance zone to the density of the absorbent material in the high density areas may be from 1.5 to 4.

The high density areas may be oblong areas.

Oblong high density areas may have a density gradient provides stiffness and rigidity to the absorbent core where needed and at the same time the required absorption properties.

Oblong high density areas may have a density gradient extending from the front edge of the coherent area and/or from the back edge of the coherent area.

Oblong high density areas may have a density gradient in the back portion of the coherent area which decreases in a direction towards the back edge of the coherent area.

Oblong high density areas may have a density gradient in the front portion of the coherent area which decreases in a direction towards the front edge of the coherent area.

The density of the absorbent material in oblong high density areas may increase in a direction from the front edge of the coherent area to a mid-section of the coherent area and/or in a direction from the back edge of the coherent area to a mid-section of the coherent area.

The density may increase in oblong high density areas from the front edge of the coherent area to the mid-section of the coherent area with from 10 $kg/m^3$ to 125 $kg/m^3$, such as with from 30 $kg/m^3$ to 70 $kg/m^3$.

The density may increase in oblong high density areas from the front edge of the coherent area to the mid-section of the coherent area with 1 $kg/m^3$ to 5 $kg/m^3$ for each 10 mm.

The density may increase in oblong high density areas from the back edge of the coherent area to the mid-section of the coherent area with from 10 $kg/m^3$ to 125 $kg/m^3$, such as from 30 $kg/m^3$ to 70 $kg/m^3$.

The density may increase in oblong high density areas from the back edge of the coherent area to the mid-section of the coherent area with 1 $kg/m^3$ to 5 $kg/m^3$ for each 10 mm.

Oblong high density areas may have a width of from 3 mm to 30 mm, such as from 5 mm to 20 mm.

Oblong high density areas may have a length of from 50 mm to 400 mm, such as from 70 mm to 300 mm or from 100 mm to 200 mm.

Oblong high density areas may extend in the longitudinal direction substantially from the front edge to the back edge of the coherent area.

Oblong high density areas may be arranged alternating in the transverse direction with longitudinally extending low density areas of absorbent material.

Oblong low density areas may have a width of from 0.5 mm to 5 mm.

The density of the absorbent material in oblong low density areas may be 50 $kg/m^3$ or less.

Oblong low density areas may have a length of from 50 mm to 400 mm, such as from 70 mm to 300 mm or from 100 mm to 200 mm.

Oblong high density areas may have, in combination, a width of from 3 mm to 30 mm, such as from 5 mm to 20 mm and a length of from 50 mm to 400 mm, such as from 70 mm to 300 mm or from 100 mm to 200 mm and may be arranged alternating with low density areas having a length equal to the length of the oblong high density areas and a width of from 0.5 mm to 5 mm, such as from 1.5 mm to 3 mm.

Oblong high density areas may have a length to width ratio of from 2 to 135, such as from 5 to 100 or from 15 to 70.

The density of the absorbent material in oblong high density areas may be from 130 $kg/m^3$ 25 to 300 $kg/m^3$, such as from 140 $kg/m^3$ to 210 $kg/m^3$.

The width of the coherent area may decrease in a direction towards the back edge of the coherent area.

The back portion of the absorbent article may comprise a conformance zone comprising absorbent material, the absorbent material in the conformance zone having a lower density than the absorbent material in the oblong high density areas.

The density of the absorbent material in oblong high density areas may be 10-90% higher than the density of the absorbent material in the conformance zone, such as 20-70% higher than the density of the absorbent material in the conformance zone.

The coherent area may comprise at least one area which is free or substantially free from absorbent material. An area which is free of substantially free from absorbent material may be an opening or a channel arranged in the coherent area.

The absorbent component as disclosed herein may comprise a single core layer.

The absorbent article as disclosed herein may comprise a single core layer.

The core cover may have an upper side and a lower side and the absorbent component may comprise a sealing arrangement joining the upper and lower sides of the core cover.

The sealing arrangement may comprise at least one sealed channel extending in the longitudinal direction of the absorbent article, the sealed channel being free or substantially free from absorbent material. The sealed channels have seals extending therein, the seals joining the upper and the lower side of the core cover within the sealed channels.

The coherent area of the absorbent component may comprise two sealed channels in the crotch portion of the absorbent article, the channels extending in the longitudinal direction of the absorbent component. A central segment may be defined in the absorbent component between the sealed channels. The two sealed channels may be symmetrically arranged on each side of the central longitudinal axis with the central segment extending in the longitudinal direction between the sealed channels.

The density of absorbent material in the central segment in the crotch portion of the absorbent article may be 5-70% higher than in oblong high density areas, such as 10-50% higher than in oblong high density areas.

The sealed channels may be permanent channels, implying that the seals joining the upper and lower sides of the core cover remain unbroken during normal use of the absorbent article. Alternatively, the seals may be temporary seals which are released as the core absorbs fluid and swells.

Permanent seals in the sealed channels restrain the cover material and prevent the absorbent material in the absorbent component from expanding into and closing the sealed channels upon wetting of the absorbent component. The channels may be free from absorbent material.

Temporary seals break open under the influence of fluid and/or the forces acting on the seals as the absorbent material absorbs fluid and swells. The freed channels may then serve as auxiliary expansion space, allowing the absorbent material to swell and expand laterally into the channels.

Oblong high density areas in the coherent area may at least partly extend along the sealed channels. This will always be the case for oblong high density areas being arranged in the crotch portion of an absorbent article as disclosed herein and having sealed channels arranged in the crotch portion.

The absorbent article may further comprise two side seams being arranged along longitudinal side edges of the absorbent component. In a coherent area having two sealed channels, a center segment having a first width is defined in the absorbent component between the sealed channels, and two side segments each having a second width are defined in the absorbent component outside each channel seal between each channel seal and a corresponding one of the side seams.

The absorbent component in the crotch portion may be configured so that 33 to 41 weight % of the absorbent material is in the center segment and 25 to 33 weight % of the absorbent material is in each one of the side segments.

When defining that the total amount of absorbent material in a center segment located between two sealed channels is generally equal to, or greater than the total amount of absorbent material in each one of the side segments, is meant that the total weight of the absorbent material in the center segment is generally equal to, or greater than, the total weight of the absorbent material in each one of the side segments.

The provision of sealed channels in the absorbent component contributes to improving fit, comfort and function of the absorbent article in its wet condition. The crotch portion of the absorbent article, and in particular a segment between two sealed channels, may be configured to develop a higher stiffness as compared with the remaining parts of the absorbent core. There is a well-known problem with sagging in the crotch portion of an absorbent article as the article absorbs liquid which accumulates in the crotch portion. The sagging problem will gradually increase as the amount of liquid absorbed by the article increases. An absorbent article, as disclosed herein and being provided with at least two permanently sealed channels, may be constructed so that the stiffness in the segment of the absorbent component which is located between the sealed channels increases gradually with the amount of liquid absorbed by the article. Initially, when only a small amount of liquid has been absorbed, the problem with sagging is negligible, and therefore the stiffness in the center segment does not need to be high. As the amount of absorbed liquid increases, the problem with sagging increases proportionally, and so a higher stiffness in the center segment is desirable to counteract the weight of the absorbed liquid in the crotch portion.

Furthermore, according to the present disclosure, absorbent side segments arranged between side seams of the absorbent component and sealed channels may not, or at least not to any substantial extent, increase its stiffness in wet condition. The absorbent side segments will ensure that the total absorbent capacity in the crotch portion is sufficient while remaining relatively soft and pliable, as compared to the stiffened portion or portions located between sealed channels. According to the present disclosure, an absorbent article may be obtained having a reduced tendency for sagging while at the same time having sufficient absorption capacity in the crotch portion and also being comfortable to wear for the user.

The core cover enclosing a central segment located between two permanently sealed channels defines and limits the expansion space for the absorbent material in the central segment. Thereby, the stiffness of the central segment will increase as the absorbent material absorbs liquid and swells during use of the article. In the absorbent articles as disclosed herein, it is not necessary that the expansion space is completely closed around the central segment or segments between the sealed channels in order to achieve the stiffening effect, only that the swelling of the absorbent material in the central segment or segments is restricted, at least in the transverse direction of the absorbent article. The ends of a central segment may be open such that fluid may pass in the longitudinal direction out of the central segment.

The front, back and crotch portion of the absorbent article may each form about a third of the length of the absorbent article. The absorbent core may be in the crotch portion and extend at least partially into the front and back portions of the absorbent article. The core may extend further into the front portion than into the back portion of the absorbent article.

The core comprises an absorbent component enclosed by a core cover. Accordingly, an absorbent component is a part of the absorbent article which is enclosed in a core cover. The absorbent component may constitute all or part of the absorbent core, as set out herein.

The absorbent component which is enclosed by the core cover, may comprise both the coherent area of the absorbent core and a conformance zone or only the coherent area of the absorbent core. In the latter case, a conformance zone may be provided as a separate component which may or may not be enclosed by a core cover.

An absorbent material composition may be the same in the coherent area and in the conformance zone. The absorbent material may comprise absorbent cellulose fibres, such as cellulose pulp fibers. The cellulose pulp fibers may be mixed with superabsorbent polymer material. The superabsorbent polymer material may be in any suitable form as known in the art, such as in the form of particles (including granules), fibers, flakes, etc.

In the coherent area of the absorbent component, the absorbent material is interconnected such that there are unbroken fluid distribution paths within the absorbent material in the longitudinal direction from the front edge of the coherent area to the back edge of the coherent area as well as in the transverse direction from one side edge of the coherent area to the other side edge of the coherent area. The coherent area extends at least in the front portion and the crotch portion of the absorbent article and extends in the transverse direction over the full width of the absorbent component inside the core cover. Thus, fluids which are absorbed by the absorbent material in the coherent area of the absorbent component can be efficiently distributed in the core component both in the longitudinal direction and in the transverse direction e.g., under the action of capillary forces within the interconnected absorbent material in the coherent area of the absorbent component. The coherent area may be framed by absorbent material such that any channel therein stops short from the front edge, the back edge, the first side edge and the second side edge of the coherent area.

Oblong high density areas are regions of the absorbent core in which absorbent material has been accumulated to provide absorption of body liquids where needed in the article and to provide rigidity to the absorbent core.

Oblong high density areas may have a greater thickness than the parts of the coherent area which are not occupied by oblong high density areas, such as the oblong low density areas. The thickness in the oblong high density areas may also be greater than the thickness of the conformance zone. Due to the accumulation of absorbent material in the oblong high density areas, the oblong high density areas have a higher basis weight than the parts of the coherent area which are not occupied by the oblong high density areas. The basis weight of the oblong high density areas may also be higher than the basis weight of the conformance zone. The absorbent material in the oblong high density areas have a higher density than the parts of the absorbent material in the coherent area which are not occupied by the oblong high density areas, such as the oblong low density areas between the oblong high density areas. The absorbent material in the oblong high density areas may also have a higher density than the density in an optional conformance zone. The absorbent material in the oblong high density areas may have any combination of greater thickness, higher basis weight and higher density than the absorbent material in parts of the coherent area which are not occupied by the oblong high density areas.

Oblong high density areas may extend in the longitudinal direction of the absorbent article, all the way or substantially all the way from the front edge to the back edge of the coherent area.

The coherent area may be a primary absorption area of the absorbent article and is configured to provide a major part of the absorption capacity of the absorbent article. The coherent area together with the conformance zone may ascertain that the liquid which reaches the absorbent article during use is safely absorbed, distributed and retained by the absorbent core. The coherent area may have any suitable shape, such as rectangular shape, hourglass shape, etc.

A conformance zone as disclosed herein offers efficient supplementary absorption of a relatively smaller amount of liquid which is not absorbed by the primary absorption material in the coherent area of the absorbent core.

The conformance zone, constitutes a secondary absorption area of the absorbent article and generally has a considerably lower absorption capacity than the coherent area of the absorbent core. As disclosed herein, the conformance zone may have the absorbent material evenly or substantially evenly distributed in a uniform or substantially uniform layer. The conformance zone may be formed from the same absorbent material as the coherent area of the absorbent core.

In addition to providing a highly conformable back portion of the absorbent article, the conformance zone saves material while still providing the absorbent article with appropriate absorbent capacity where needed. When the conformance zone is non-contiguous with the coherent area. A conformance zone is considered to be non-contiguous with the coherent area if there is a distance between the back edge of the coherent area and a front edge of the conformance zone. A non-contiguous conformance zone may alternatively be described as being detached, separate or independent from the coherent area.

As disclosed herein, the conformance zone may be symmetrically arranged in relation to the longitudinal axis such that the conformance zone is mirror symmetric about the central longitudinal axis through the absorbent article. The conformance zone may have a triangular shape, a D-shape, a W-shape or a rectangular shape, including a square shape. When triangular or D-shaped, the conformance zone has a shape which narrows in a direction towards the back end edge of the absorbent article such that a width of the conformance zone adjacent the back edge of the coherent area of the absorbent core is greater than a width of the conformance zone adjacent the back end edge of the absorbent article. The width of the conformance zone may decrease continuously or in equally sized steps, as in a triangular conformance zone. The width of the conformance zone may be constant in a front area closest to the back edge of the coherent area and decrease only at the back end of the conformance zone, as in a D-shaped conformance zone. The width of the conformance zone may be constituted by two or more rectangular sub-zones of different width with a more forward sub-zone having a greater width than a more rearward sub-zone or may have any other shape with a smaller width at the back part of the conformance zone than at the front part of the conformance zone.

A triangular or D-shaped conformance zone has been found to be in agreement with spreading patterns observed in user tests, wherein means for liquid absorption has been shown to be primarily needed in a central longitudinal area of the back portion of the absorbent core, with less or no absorption capacity needed near the longitudinal sides of the back portion of the absorbent core.

The back edge of the coherent area may be a non-linear edge and may have at least one aberration, such as one or more protrusions extending away from a straight base line or a baseline having an even curvature. The back edge of the coherent area may have the form of a baseline from which evenly distributed protrusions extend in a direction toward the back end edge of the absorbent article.

The protrusions of the back edge of the coherent area may be in the form of semi-circles extending longitudinally away from the front end edge of the absorbent article and towards the back end edge of the absorbent article.

The absorbent article may comprise leg elastic elements extending along all or a part of each longitudinal side edge of the absorbent article. If one or more longitudinally extending channel is provided in the crotch portion of the absorbent article, the leg elastic elements may have a greater length in the longitudinal direction of the absorbent article than the length of the one or more longitudinally extending channel.

The leg elastic elements may extend in the longitudinal direction of the article in the crotch portion of the absorbent article and in part of the front portion and/or part of the back portion of the absorbent article. The leg elastic elements may have a greater extension in the back portion than in the front portion.

The leg elastic elements may cooperate with features of the absorbent component such as the oblong high density areas and the optional sealed channels as disclosed herein, to promote shaping and fit of the absorbent article during use.

A ratio of a width of a center segment of the absorbent component as measured in the transverse direction between two sealed channels and a distance in the transverse direction between the leg elastic elements may be from 0.10 to 0.30, from 0.15 to 0.25 or from 0.18 to 0.22.

The article may comprise a waist elastic feature located in the back portion at the back end edge of the absorbent article. A waist elastic feature, together with leg elastic elements and the absorbent component may cooperate with the arrangement of a stiffening central segment located between two sealed channels and two side segments to provide improved fit of the article during use. In addition to or instead of a waist elastic feature in the back portion of the absorbent article, a waist elastic feature may be located in the front portion of the absorbent article. Waist elastic features may extend only partly along the front and/or the back end edge or may extend the full length of the front and/or the back end edge, i.e. from the first side edge to the second side edge of the absorbent article.

A core cover as disclosed herein may be formed by a separate upper core cover layer forming the upper side of the core cover and a separate lower core cover layer forming the lower side of the core cover, the upper and lower core cover layers together enclosing the absorbent component. A sealing arrangement may be provided for joining the upper and lower sides of the core cover at the edges of the core component. The disclosure is not limited to core covers comprising two separate core cover layers. The core cover may be formed from a single material layer. In such case the absorbent component may be enclosed by one core cover layer which is wrapped around the absorbent component or which is formed as a tubular structure into which the absorbent component is inserted. Furthermore, the core cover may be made from more than two core cover layers. The core cover may be sealed only in the longitudinal direction of the absorbent article, leaving the core cover open in both a front end of the core cover and in a back end of the core cover. Alternatively, the core cover may be sealed at one or both of the front end and the back end of the core cover. In the latter case, the absorbent component is completely enclosed inside the core cover.

In the absorbent article as disclosed herein, both the upper core cover layer and the lower core cover layer may be liquid-permeable cover layers together forming a liquid permeable core cover. The upper core cover layer and optionally also the lower core cover layer may be a hydrophilic layer. Hydrophilicity may be accomplished by incorporating inherently hydrophilic fibers in the core cover layer, such as cellulose fibers or regenerated cellulose fibers, e.g. wood pulp fibers, cotton, flax, hemp, viscose, etc. as known in the art. Hydrophilicity may also be accomplished by treating inherently hydrophobic materials such as polymeric films and fibers, e.g. polyolefins such as polyethylene and polypropylene, polyesters, etc. to render them hydrophilic and wettable.

The lower core cover layer may be liquid impermeable and/or hydrophobic

The basis weight of the core cover material may be in the range of from 5 g/m² to 20 g/m².

The core cover material may be made of thermoplastic polymer material, such as polyolefin, polyesters, polyamide and combinations thereof. The core cover material may be nonwoven material. The nonwoven material may be made of thermoplastic polymer material fibers or filaments. The nonwoven layer may be formed by any of a variety of different processes, such as spunbonding, airlaying, meltblowing or bonded carded web formation processes. The nonwoven layer may be made of co-formed lamina of nonwoven materials such as an SMS (spunbond/meltblown/spunbond) nonwoven material or an SS (spunbond/spunbond) nonwoven material. The thermoplastic polymer materials in the nonwoven layer may be polypropylene or bicomponent fibers of polypropylene and polyethylene, or of a combination of such materials.

As set out herein, the absorbent article may comprise a single core layer.

An absorbent component as disclosed herein may be constituted by one single absorbent component layer which is wrapped in a core cover having an upper side and lower side.

Absorbent components comprising two or more layers are also contemplated for the absorbent cores as disclosed herein.

The absorbent component may have a rectangular shape. A rectangular absorbent component may have the advantage of being easy to manufacture and enclose by a core cover.

The absorbent component may comprise a mixture of absorbent cellulose fibers, such as cellulose pulp fibers (pulp material) and superabsorbent polymer material in the form of particles, granules, fibers, flakes, etc. The absorbent material in the absorbent component, at least in the crotch portion, may be constituted by 50-100 weight % superabsorbent material and 0-50 weight % pulp material, or 70-100 weight % superabsorbent material and 0-30% pulp material.

The composition of the absorbent material may be the same in the coherent area and in an optional conformance zone. Hence, a mixture of superabsorbent material and pulp material may be the same in the coherent area and in the conformance zone.

The total absorbent capacity per cubic centimeter of the coherent area of the absorbent component in dry condition may be at least 15 g/cm³, or at least 25 g/cm³ or at least 35 g/cm³.

The pulp material in the coherent area of the absorbent component may have a basis weight which is in the interval of 50-400 g/m² and the superabsorbent material may have a basis weight which is in the interval of 100-900 g/m².

The thickness of the coherent area of the absorbent component in dry condition, measured with an applied pressure of 0.5 kPa, may be in the range of from 1.0 to 5.5 mm or from 2.0 to 4.5 mm. A representative mean value may be obtained by measuring on several parts of the absorbent component.

The absorbent component may be formed using an air forming process, such as an air forming process carried out on an air forming drum, also referred to as a vacuum forming drum. The air forming drum operates by application of internal suction in the forming drum to draw flows of air suspended absorbent material into forming molds arranged on the surface of the forming drum.

The forming drum may have several forming molds arranged on the outer surface into which the absorbent material is deposited for continuously forming absorbent components. The shape and size of the forming molds determine the shape and size of the absorbent components. Each forming mold has a foraminous air permeable bottom on which the air suspended absorbent material is collected and accumulated as the air is drawn off into the interior of the forming drum. The amount of material deposited in different parts of the mold may be controlled by controlling the air flow through the foraminous bottom. To this end, the foraminous bottom of the mold may have different air permeability in different portions of the mold which may be accomplished by arranging masking plates in different parts of the mold and/or by shaping the foraminous bottom to create a mold with varying depth, corresponding to an absorbent component having different thickness in different parts. A first part of the mold may be arranged to produce the coherent area of the absorbent component as set out herein. The bottom of the first part of the mold may then comprise grooves corresponding to where oblong high density areas of accumulated material are to be formed which will form oblong high density areas in the coherent area of the absorbent component and/or one or more blocked areas where channels are to be formed in the absorbent component. A second part of the mold is arranged to produce the conformance zone and has a blocking plate having openings arranged therein. The presence of blocking plate(s) in the second part of the mold serves to decrease the air permeability in this area of the mold and causes a greater part of the air flow and concomitantly a greater part of the air suspended absorbent material to be drawn towards and collected in the first part of the forming mold. It also creates the area substantially free from absorbent material vertically separating the coherent area and the conformance zone.

The disclosure may be varied within the scope of the appended claims. For example, the materials and dimensions used for the different layers forming an absorbent article as disclosed herein may be varied, as indicated above. The absorbent article may further include any useful component or feature as known in the art such as fluid acquisition and distribution components, leg elastics, standing gathers, crotch and waist elastics, side panels, fastening systems, wetness indicators, skin care agents, disposal means, etc., as known in the art and depending of the type of absorbent article intended.

BRIEF DESCRIPTION OF THE DRAWINGS

Preferred exemplary embodiments of the absorbent articles as disclosed herein will be further explained hereinafter with reference to the appended drawings wherein.

DETAILED DESCRIPTION OF THE PREFERRED EXEMPLARY EMBODIMENTS

Different aspects of the present disclosure will be described more fully hereinafter with reference to the enclosed drawings. The embodiments disclosed herein can, however, be realized in many different forms and should not be construed as being limited to the aspects set forth herein.

It is to be understood that the drawings are schematic and that individual components, such as layers of material are not necessarily drawn to scale.

Figure 1:
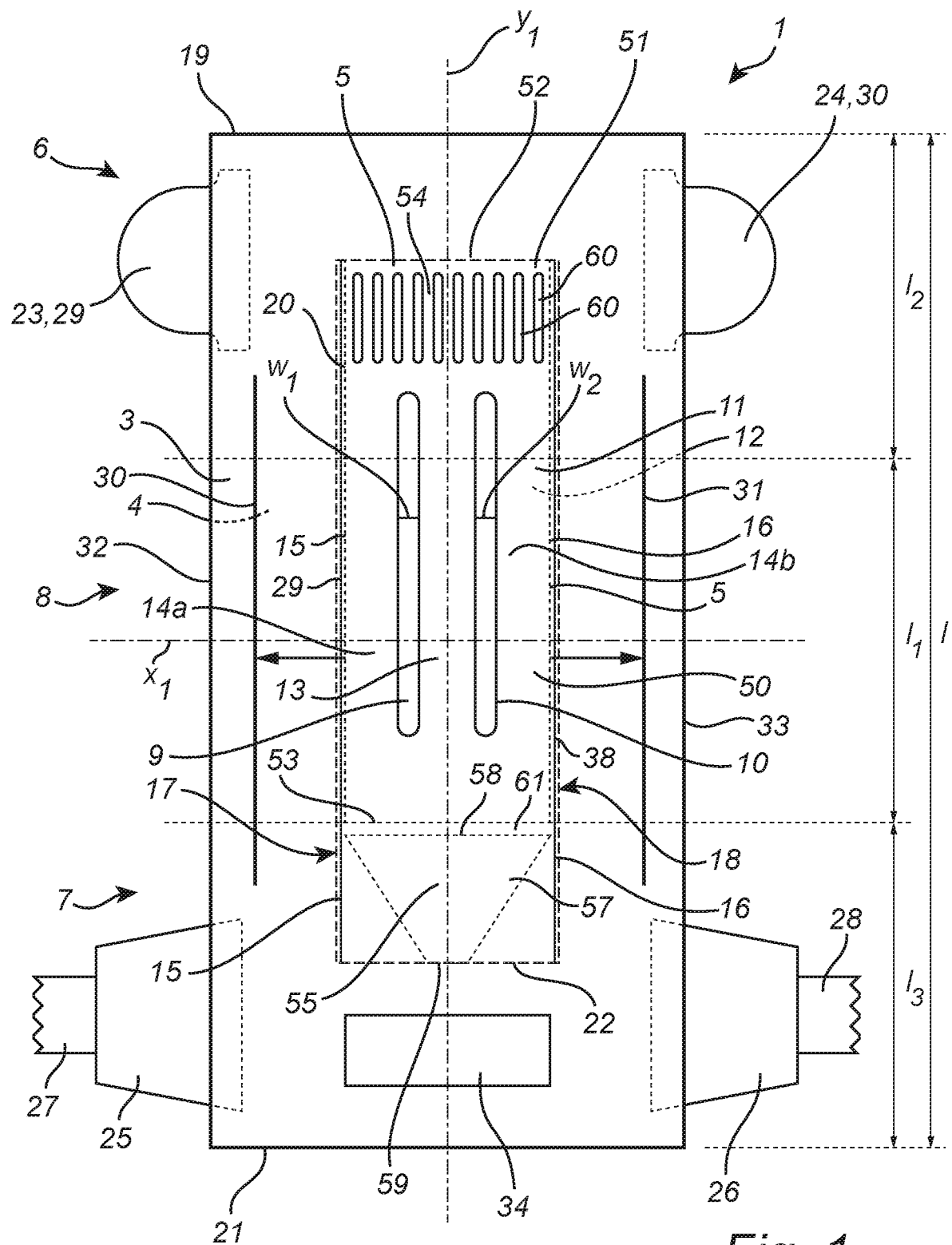
FIG. 1 shows a view from above of an absorbent article in the form of a diaper.

With initial reference to FIG. 1, there is shown an absorbent article 1 in the form of a baby diaper. The absorbent article 1 is shown in FIG. 1 in an unfolded and flat state with all elastic elements in an extended state.

The absorbent article 1 is seen from the surface which will be facing a wearer's body when the article is being worn and comprises a liquid-permeable topsheet 3, a liquid-impermeable backsheet 4 and an absorbent core 5 which is sandwiched between the topsheet 3 and the backsheet 4. The topsheet 3 is arranged at the inner or wearer-facing surface of the absorbent article 1, whereas the backsheet 4 is arranged at the outer or garment-facing surface of the absorbent article 1. Furthermore, as illustrated in FIG. 1, both the topsheet 3 and the backsheet 4 may extend laterally outside of the absorbent core 5 along the entire perimeter of the absorbent article 1. Alternatively, the topsheet 3 and the backsheet 4 may be generally coextensive with the absorbent core 5 or only one of the topsheet 3 and the backsheet 4 may extend outside the perimeter of the absorbent core 5. It is also conceivable that the topsheet 3 and the backsheet 4 extend outside of the absorbent core only along parts of the perimeter of the absorbent article, such as only along the side edges or only along one or both end edges or along the side edges and only one of the end edges.

The absorbent core 5 shown in FIG. 1 has a rectangular design. However, as set out herein, the disclosure is not limited to this design and it is to be understood that the absorbent core may have any useful shape within the scope of the invention.

The topsheet 3, backsheet 4 and the absorbent core 5 may consist of any materials suitable for their purposes, as will be discussed in further detail below.

As shown in FIG. 1, the absorbent article 1 has a longitudinal direction along a central longitudinal axis y1 and a transverse direction along a central transverse axis x1, which is perpendicular to the longitudinal axis y1. Furthermore, the absorbent article 1 may be defined as being divided into a front portion 6 having a length $l_2$, a back portion 7 having a length $l_3$ and a crotch portion 8 having a length $l_1$. Each of the front, back and crotch portion 6, 7, 8 of the absorbent article may form about a third of the length of the absorbent article 1.

The front portion 6 has a front waist edge constituting a front end edge 19 of the absorbent article 1 and the back portion 7 has a back waist edge constituting a back end edge 21 of the absorbent article 1. Leg edges are formed by longitudinally extending side edges 32,33 of the absorbent article 1. The front portion 6 is the part of the absorbent article which is intended to be oriented in a direction towards the belly of the wearer during use of the absorbent article 1 and the back portion 7 is the part of the absorbent article which is intended to be oriented in a direction towards the buttocks of the wearer.

The absorbent article 1 in FIG. 1 is an open-type diaper having front gripping tabs 23, 24 extending from the side edges 32, 33 at the front end edge 19 of the absorbent article 1 and back fastener tabs 25, 26 extending from the side edges 32, 33 at the back end edge 21 of the absorbent article 1. When applying the absorbent article 1 to a wearer, the back fastener tabs 25, 26 are brought forward towards the wearer's belly and are attached with fastener elements 27, 28, such as hook-type fastener elements onto mating fastener elements such as loop-type fastener elements which are provided on the outer surface of the front portion 6 of the absorbent article 1.

It is to be understood that male fasteners, such as hook-type fasteners may instead be placed at the front of the article while female fasteners may be placed at the back of the article. Furthermore, the fastening arrangement may differ from that shown in the FIGS. and may be of any useful kind as known in the art. Accordingly, fastener belts, girdles, adhesive fastening systems, etc. may be used. It should also be noted that the fastening system is optional to the absorbent article 1, as the article may be designed for use as an absorbent insert, worn inside a pair of supportive pants or ordinary underpants. Such articles may be provided with fastening adhesive arranged on the outer surface of the backsheet, to allow the article to be fastened inside the pants. Furthermore, the absorbent article may be a pant-type article which is provided in a pre-assembled configuration, with closed side seams. Such articles may nevertheless be provided with a fastening system, to allow the article to be opened and reclosed.

The absorbent core 5 comprises an absorbent component 50 which is sandwiched between an upper core cover side 11 and a lower core cover side 12. The core cover is a component of the absorbent article 1 which is provided in addition to the topsheet 3 and the backsheet 4. The absorbent component 50 has a front edge 52 and a back edge 22.

The absorbent component 50 comprises a coherent area 51 which is disposed forward in the absorbent article 1 with a forward part of the coherent area 51 being located in the front portion 6 and a rearward part of the coherent area 51 being located in the crotch portion 8 of the absorbent article 1 and optionally extending also into the back portion 7 of the absorbent article 1. The coherent area 51 has a front edge 52, a back edge 53, a first side edge 29 and a second side edge 38. As can be seen in FIG. 1, the width of the absorbent core 5 is the same as width of the absorbent material inside the core cover 11, 12 of the absorbent component 50 within the coherent area 51. This width is defined by the width of the coherent area 51 between the first side edge 29 and the second side edge 38. The coherent area 51 is coherent with interconnected fluid distribution paths running all the way from the first side edge 29 of the coherent area 51 to the second side edge 38 of the coherent area 51 implying that liquid may travel along unbroken paths from one side edge 29 to the other side edge 38 of the coherent area 51. The back portion 7 of the absorbent article 1 comprises a conformance zone 55 which is placed behind the coherent area 51 as seen in a direction towards the back end edge 21 of the absorbent article 1.

The coherent area 51 of the absorbent core 5 comprises high density areas 60, the high density areas 60 may be oblong as in FIG. 1, extending in the longitudinal direction within the material in the front portion of the coherent area 51 towards the back end edge 21 of the absorbent article 1. The oblong high density areas 60 are regions of the absorbent core 5 in which absorbent material has been accumulated such that longitudinally extending striations are formed in the material of the coherent area 51. The number of oblong high density areas in FIG. 1 is 11, but may be from 3 to 30 oblong high density areas 60.

The oblong high density areas 60 may each have a density gradient with increasing density in a direction from the front edge 52 of the coherent area 51 towards a mid-section of the coherent area 51.

The density may increase in the oblong high density areas 60 with from 10 $kg/m^3$ to 125 $kg/m^3$.

The density may increase in the oblong high density areas 60 with 1 $kg/m^3$ to 5 $kg/m^3$ for each 10 mm.

The density of the absorbent material in the oblong high density areas 60 may be at least 130 $kg/m^3$ and below 300 $kg/m^3$. The oblong high density areas 60 have a width of 3 to 30 mm, such as 5 to 20 mm. The high density areas 60 are delimited in the transversal direction by low density areas 54 of absorbent material. The oblong low density areas 54 may have a width of from 0.5 mm to 5 mm. The density of the absorbent material in the oblong low density areas may be 50 $kg/m^3$ or less.

The length of the oblong high density areas 60 and the oblong low density areas 54 may be from 50 to 400 mm, such as from 70 to 300 mm or from 100 to 200 mm. In the embodiment shown in FIG. 1, the oblong high density areas 60 and the intervening oblong low density areas 54 are arranged only in the front portion 6 of the absorbent article and have a length in the order of 70 mm. As disclosed herein, the oblong high density areas 60 and the oblong low density areas 54 may in addition to being arranged in the front portion 6 of the article 1 be arranged also in the crotch portion 8 of the article 1 or only in the crotch portion 8 of the article 1.

The conformance zone 55 as shown in FIG. 1 is non-contiguous with the coherent area 51 of the absorbent component 50 as the conformance zone 55 is arranged at a distance from the coherent area 51. The V-shaped area 57 has its base arranged at a distance from the back edge 53 of the coherent area 51 and its tip 59 arranged on the central longitudinal axis y1 of the absorbent article and facing the back end edge 21 of the absorbent article 1. The coherent area 51 and the conformance zone 55 are separated vertically by an area 61 substantially free from absorbent material. The area 61 separating the coherent area 51 and the conformance zone 55, as seen in FIG. 1, traverses the whole width of the absorbent component 50. The area substantially free from absorbent material 61 may have a basis weight of less than 50 gsm, such as less than 25 gsm, such as less than 5 gsm and may have a width of 2-30 mm, 2-20 mm such as 5-10 mm.

The conformance zone 55 of the article 1 illustrated in FIG. 1 comprises absorbent material and the zone may be without gaps or areas being free from absorbent material. The absorbent material in the conformance zone 55 may have a uniform or substantially uniform distribution of absorbent material. The absorbent material in the conformance zone 55 may not comprise individual clusters of absorbent material having a diameter larger than 10 mm. The density of the absorbent material in the conformance zone 55 may be substantially uniform. The conformance zone 55 may comprise a substantially homogenous mixture of superabsorbent material and cellulose fibers. The mixture of superabsorbents and cellulosic fibers in the conformance zone may have a basis weight coefficient of variation of at most 20%, as measured according to the method for measuring basis weight evenness provided in this disclosure. The ratio of basis weight of the absorbent material in the conformance zone 55 to the basis weight in the high density areas 60 may be from 1.5 to 4. The ratio of the density of the absorbent material in the conformance zone 55 to the density of the absorbent material in the high density areas 60 may be from 1.5 to 4.

In the absorbent article 1 as shown in FIG. 1, the conformance zone 55 is enclosed by the upper and lower sides of the core cover 11, 12 and forms part of the absorbent component 50. The planar shape and size of the absorbent component is defined by the planar shape and size of the core cover. As disclosed herein, the core cover may be formed by two separate sheets of material which are sealed at least along their longitudinally extending side edges and optionally also along one or both of the transversely extending end edges. Alternatively, the core cover may be formed by a bi-folded sheet of material which may be folded in the longitudinal direction and sealed at least along the side edges which are opposite to the fold.

The coherent area 51 of the absorbent component 50 which is shown in FIG. 1 comprises oblong high density areas 60 extending in the longitudinal direction in a front portion of the coherent area 51.

The density of absorbent material may be higher in the oblong high density areas 60 than in the conformance zone 55 in the back portion 7 of the absorbent article 1.

The absorbent component 50 which is shown in FIG. 1 is formed with two longitudinally extending and generally straight sealed channels 9,10 in which the upper core cover side 11 is joined to the lower core cover side 12 by seals extending along the sealed channels 9,10. The seals may be provided as bond lines consisting of bonding elements arranged in a bond pattern. A width of each bond line may be less than a width of the corresponding sealed channel 9, 10 in which the bond line is arranged. Thereby, a slack is formed in the core cover material between the edge of the bond line and the edge of the sealed channel in which the bond line is placed. Such slack may be provided to allow expansion room for the absorbent material arranged on either side of the bond lines. The slack may be smaller on the inner side of each sealed channel 9,10 which is facing towards the centre of the absorbent article, and larger on the outer side of each sealed channel 9,10 which is facing towards the side edges of the absorbent article 1.

As set out herein, the disclosure is not limited to a core wrap comprising two core cover layers. The core cover may be of one single material layer. The absorbent component may be enclosed by one core cover layer folded in two, or enclosed by a continuous core cover sheet, thereby providing upper and lower core cover sides for wrapping the absorbent component.

The upper core cover side 11 and the lower core cover side 12 may be attached to each other by any useful means as known in the art, for example, by thermo-mechanical bonding, such as thermo-sealing, ultrasonic bonding, an adhesive or adhesives, stitching or the like, or combinations of the same.

The sealed channels 9,10 constitute sections of the absorbent component 50 which are free from absorbent material. Absorbent free channels may be obtained by manufacturing the absorbent component 50 using a mat forming process during which absorbent material is omitted from the areas which correspond to the sealed channels 9,10. In this manner, no absorbent material will be present in the sealed channels 9,10. The presence of absorbent material in the sealed channels 9,10 may negatively influence the strength of the seals between the upper and lower core cover sides 11, 12 and should be avoided.

As shown in FIG. 1, the absorbent component 50 may be divided into a central segment 13 located in the crotch portion 8 between the sealed channels 9,10 and two side segments 14*a*, 14*b*. The sealed channels 9,10 are consequently configured so that they separate the three segments 13, 14*a*, 14*b* from each other in the crotch area 8.

The absorbent component 50 may be generally rectangular and may comprise two generally straight sealed channels 9, 10 which extend generally parallel to the longitudinal axis y1. The seals joining the upper and lower core cover sides 11, 12 have a corresponding first channel sealing width w1 and a second channel sealing width w2. The disclosure is not limited to a rectangular absorbent component 50 and generally straight sealed channels 9, 10, i.e. other geometrical configurations may be used.

Furthermore, the central segment 13 is defined in the absorbent component 50 between the sealed channels 9, 10. The two side segments 14*a*, 14*b* are defined in the absorbent component 50 outside each sealed channel 9, 10. More precisely, the first side segment 14*a* is positioned between the first sealed channel 9 and a first side seam 15, whereas the second side segment 14*b* is positioned between the second sealed channel 10 and a second side seam 16. The side seams 15, 16 are configured for joining the upper core cover side 11 to the lower core cover side 12, suitably by means of ultrasonic welding or other relevant technologies as described above with reference to the seals joining the upper cover side 11 and the lower cover side 12 in the sealed channels 9, 10. The sealed channels 9, 10 may be permanently sealed channels 9, 10 as disclosed herein, implying that the central segment 13 may swell and form a stiffening element between the sealed channels 9, 10. Alternatively, the sealed channels may be temporarily sealed channels 9,10 in which the seals arranged in the sealed channels 9,10 between the upper and lower core cover sides 11, 12 break when the core 5 absorbs liquid and swells, so that the absorption material may expand into the released channels.

Furthermore, the side seams 15, 16 extend along each side of the absorbent component 50, inward of and along a first side edge 17 and a second side edge 18 of the absorbent component 50.

As mentioned, the length l1 of the crotch portion 8 may be equal to the length of the sealed channels 9, 10, i.e. the sealed channels 9, 10 may be arranged only in the crotch portion 8. However, the side seams 15, 16 may not just be positioned along the crotch portion 8 but may also extend into the front portion 6 and/or the back portion 7 as set out in more detail below.

The absorbent article 1 in FIG. 1 also has leg elastic elements 30,31 extending along each longitudinal side edge 32,33 of the absorbent article 1. The leg elastic elements 30,31 have a greater length in the longitudinal direction than the length of the sealed channels 9, in the longitudinal direction. Accordingly, the leg elastic elements have an extension not only in the crotch portion 8 but also in a part of the front portion 6 and the back portion 7. The leg elastic elements 30, 31 have a greater extension in the back portion 7 than in the front portion 6, as seen in FIG. 1.

The absorbent article 1 also has a waist elastic element 34 located in the back portion 7 close to the back end edge 21 of the absorbent article 1. It is to be understood that also the front end edge 19 may be provided with waist elastic, if desired.

The leg elastic elements and the waist elastic element are optional features of an absorbent article as disclosed herein.

As disclosed herein, the absorbent component 50 is formed with a sealing arrangement which is constituted by the two sealed channels 9, 10 and the two side seams 15, 16. The sealing arrangement is configured so that, in the crotch portion 8, the absorbent component 50 is divided into a central segment 13 and two side segments 14*a*, 14*b*.

As disclosed herein, the absorbent material may comprise a mixture of cellulose pulp material and superabsorbent material. The absorbent component 50 may be configured so that the total amount of absorbent material of the central segment 13 between the sealed channels 9, 10 is generally equal to or greater than the amount of absorbent material in either one of the side segments 14*a*, 14*b* between each sealed channel 9, 10 and the corresponding side seam 15, 16. In an embodiment having permanently sealed channels 9,10, this means that the available space for expansion of the absorbent material in the central segment 13, as the absorbent article 1 becomes wet as it absorbs liquid during use, is less than a corresponding available expansion space for each side segment 14*a*, 14*b*. This will lead to a situation in which the central segment 13 will be stiffer than the side segments 14*a*, 14*b* when the absorbent article is in its wet condition. The stiffened central segment 13 counteracts the tendency of the wet article to sag and hang down in the crotch portion 8.

The expression "generally equal" as used above for describing the amount of absorbent material in the central segment 13 as compared with the side segments 14*a*, 14*b* should be understood as allowing for slight variations in the amount of absorbent material in the order of approximately ±5% in any part of the crotch portion 8.

A width of the central segment 13 may be defined between the sealed channels 9, 10 and a width of the absorbent component 50 may be defined between the first and second side edges 17, 18 of the absorbent component 50. The ratio of the width of the central segment 13 and the width of the absorbent component 50 may be in the range of from 0.25 to 0.45.

The width of the coherent area 51 is equal to the width of the absorbent component 50 between the first and second side edges 17, 18 of the absorbent component 50.

As disclosed herein, various types of materials may be used for the absorbent article 1. The topsheet 3 which is arranged to face the wearer of the absorbent article 1 when the article is being worn may comprise or consist of a fluid permeable nonwoven fabric, film, mesh or foam. The topsheet may be made from thermoplastic material, such as thermoplastic synthetic fibers, film or netting. The topsheet 3 may be sufficiently liquid-permeable to allow discharged body fluids to penetrate through the thickness of the topsheet 3. Also, the topsheet 3 may suitably be manufactured from a material which is compliant and soft-feeling to the skin of the wearer. The topsheet 3 may consist of a single layer or may have a laminate structure comprising a plurality of layers, for example, two or more layers. The layers may be made of the same material, or some or all of the layers may be made of different materials.

The layer of the topsheet 3 or, for the case of a laminate structure, one, some, or all layers of the topsheet may be made of a single web of material or may have portions made of different materials, e.g., within different parts of the wearer-facing surface of the topsheet.

The layer of the topsheet 3 or, for the case of a laminate structure, one, some or all layers of the topsheet may be a nonwoven material, a perforated plastic film, a plastic or textile mesh, or a liquid permeable foam layer. The layer of the topsheet 3 or, for the case of a laminate structure, one, some or all of the layers of the topsheet may be, for example, a hydrophilic, non-apertured nonwoven web of fibers, such as natural fibers, e.g., cotton or pulp fibers, synthetic fibers, e.g., polyester or polypropylene fibers, or a combination of these fibers. The topsheet may have a basis weight in the range of 8-40 g/m$^2$. However, the disclosure is not limited to topsheets having this basis weight.

Furthermore, the backsheet 4 may be constituted by a liquid-impermeable layer such as a polymeric film, for example a film of polyethylene or polypropylene. The backsheet 4 may be breathable. The materials which may be used for the backsheet 4 include thin and flexible fluid impermeable plastic films, or fluid impermeable nonwoven materials, fluid impermeable foams and fluid impermeable laminates. The backsheet 4 may be formed by a single layer, but may alternatively be formed by a multi-layered structure, i.e. a laminate, wherein at least one layer is fluid impermeable. Furthermore, the backsheet 4 may be elastic in any direction. Furthermore, the backsheet 4 may have a laminate structure comprising a liquid barrier sheet and a nonwoven layer arranged on top of each other (not shown in detail in the drawings), wherein the nonwoven layer is arranged at an outer side away from the wearer of the absorbent article 1 when worn.

The nonwoven layer may be made of thermoplastic polymer material fibers or filaments. The nonwoven layer may be formed by any of a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials. The nonwoven layer may have a basis weight in the range of 5-40 g/m$^2$.

The liquid barrier sheet may be made of a plastic material, for example a thermoplastic film material, and/or a nonwoven material. For example, the liquid barrier sheet may be formed as a plastic layer, e.g., a thermoplastic layer, or a plastic film, e.g., a thermoplastic film. Forming the liquid barrier sheet of a plastic material, such as a thermoplastic film material, allows for a particularly good printability of the liquid barrier sheet. The liquid barrier sheet may also contain paper fibers. The liquid barrier sheet may be a liquid impermeable, breathable or non-breathable layer. The liquid barrier sheet may consist of a single layer or have a laminate structure with a plurality of layers, e.g., two or more layers, three or more layers, or four or more layers. The layers of the liquid barrier sheet may be laminated, bonded or attached to each other, for example, by thermo and/or mechanical bonding, such as thermo-sealing, ultrasonic bonding, such as ultrasonic welding, an adhesive or adhesives, stitching or the like. The liquid barrier sheet may be a breathable microporous film. The microporous film may be made of a material comprising at least two basic components, namely a thermoplastic elastomeric polyolefin polymer and a filler. These components and, in some embodiments, additional other components may be mixed together, heated and subsequently extruded into a mono-layer or multi-layer film using any one of various film-producing processes, such as cast embossed, chill and flat cast, and blown film processes.

Regarding the choice of materials for the various layers in the absorbent article, the materials may be chosen with consideration for the bonding processes used when forming seals in between components of the absorbent article, such the seals in the sealed channels and the side seams. For example, if ultrasonic welding is chosen for joining the upper and lower core cover sides, the materials for the core cover may be chosen such that they can form a secure bond during ultrasonic welding, e.g. by at least one of the upper and lower side of the core cover comprising or consisting of thermoplastic polymer material.

The absorbent core 5, includes the absorbent component 50 and may include further absorbent components such as components which provide liquid acquisition and liquid distribution. The absorbent core is disposed between the topsheet 3 and the backsheet 4 to absorb the liquid, such as urine or other bodily fluids, which has passed through the topsheet 3. The absorbent component 50 may be a single-layer structure or may be a layered structure, e.g. within the coherent area. The absorbent component 50 may comprise suitable amounts of superabsorbent material. Such superabsorbent material is well known in the field of absorbent articles, and is constituted by a water-swellable and water-insoluble material which is capable of absorbing large quantities of fluid upon formation of a hydrogel. The absorbent component may contain superabsorbent material in the form of fibers or particles of absorbent polymer material. For example, the superabsorbent material may be surface cross-linked, partially neutralized polyacrylates. The superabsorbent material, e.g., the superabsorbent fibers or particles, may be mixed with other absorbent or liquid uptake material or materials, such as cellulose fluff pulp, and/or arranged in pockets or layers in the absorbent component 50. The amount of superabsorbent material and pulp in the absorbent component 50 may be from 0 to 50 weight % pulp fibers and from 50 to 100 weight % superabsorbent material, or from 0 to 30 weight % pulp fibers and from 70 to 100 weight % superabsorbent material.

The absorbent component 50 may further comprise components for improving properties of the absorbent core 5, such as core integrity and strength. For example, the absorbent component 50 may comprise a binder or binders, such as binder fibers. Resilient fibers, chemically stiffened fibers, etc. may be present in the absorbent component to counteract wet-collapse of cellulosic fibers. Such fibers may also be useful in retaining a fluid transporting capillary network in the absorbent component so that absorbent fluid may be distributed in the absorbent component and be absorbed by superabsorbent material also in parts of the absorbent component outside the initial wetting area of the absorbent article.

The core cover 11,12 may be formed by a separate upper core cover 11 layer and a separate lower core cover 12 layer. However, the disclosure is not limited to a core cover comprising two separate core cover layers. The core cover 11,12 may also be made of one single material layer. The absorbent component 50 may be enclosed by one core cover 11,12 layer which is folded in two and sealed along the open edges, or may be enclosed by a continuous, tubular core cover sheet, thereby providing upper 11 and lower core cover 12 sides for wrapping the absorbent component 5a,5b, 5c. The basis weight of the core cover 11,12 material may be in the interval of from 5 g/m² to 20 g/m². The core cover 11,12 material may be made of thermoplastic polymer material. The core cover material may be nonwoven material. The nonwoven material may be made of thermoplastic polymer material fibers or filaments. The nonwoven layer may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials.

Furthermore, the various layers and components of the absorbent article 1 may be attached by means of adhesive material, as known in the art. Such adhesive is not shown in the drawings.

One or more additional layers may be provided in the absorbent article 1. For example, an acquisition layer may be arranged between the absorbent component 50 and the topsheet 3. Such an additional layer may for example be in the form of an airlaid layer, a spunlace layer, a high-loft fiber material, an open-cell or perforated foam or any other type of material layer or combination of layers which may be used in an absorbent article to act as a liquid handling layer providing functions such as liquid acquisition, liquid absorption and liquid distribution. A liquid acquisition layer is adapted to quickly receive and temporarily store discharged liquid before the liquid can be absorbed by the absorbent component. Such acquisition layer may be composed of for example airlaid nonwoven, spunlace nonwoven, high loft nonwoven or foam materials. An airlaid nonwoven may be produced wood pulp fluff fibers which are dispersed and suspended in a fast-moving air stream and condensed onto a moving screen by means of pressure and vacuum.

With reference again to FIG. 1, each sealed channel 9, 10 may have a length l1 which corresponds to the longitudinal extension of the crotch portion 8. Each one of the sealed channels 9, 10 may have a length l1 which is between 5-50%, such as 10-50%, such as 28-38%, of the total length l of the absorbent article 1. Furthermore, each sealed channel 9, 10 may have a length l1 which is between 10-60%, such as between 20-60%, such as between 30-50%, of the length of the absorbent component 50.

A further parameter is the positioning of the sealed channels 9, 10 in the longitudinal direction of the absorbent article 1.

The position of the sealed channels 9, 10 in the longitudinal direction of the absorbent article 1 may be chosen so that each channel 9, 10 terminates at a distance from the front end edge 19 of the article 1 which is between 15-40%, such as between 22-25%, of the total length l of the article 1.

Furthermore, the topsheet may comprise at least one additive material such as a skin care composition. The additive may be located on parts of the topsheet which are disposed along the longitudinal side edges 32, 33 of the absorbent article 1 and/or along the longitudinal side edges 17, 18 of the absorbent component 50. An advantage with such placement of the additive material, is that as the parts of the absorbent article 1 which are arranged along the side edges normally will be closer to the body of the wearer of the absorbent article 1 than a longitudinally central part of the absorbent article 1, the skin care benefits of the additive may be obtained without the additive interfering with fluid acquisition through the topsheet 3 in the central part of the absorbent article 1.

FIGS. 2A-2G illustrate absorbent components 50 having different combinations of features. The absorbent components 50 shown in the examples of FIGS. 2A-2G should not be considered to be limiting to the absorbent articles as disclosed herein, as it should be understood that one or more features of the coherent area 51 in any one of FIGS. 2A-2G can be freely combined with features of the conformance zone 55 in any other of FIGS. 2A-2G.

The absorbent components 50 in FIGS. 2A-21 all have a conformance zone 55. The conformance zone 55 comprises absorbent material and the zone may comprise any of, or a combination of, the following: be without gaps or areas being free from absorbent material; the absorbent material in the conformance zone 55 may have a uniform or substantially uniform distribution of absorbent material; the absorbent material in the conformance zone 55 may not comprise individual clusters of absorbent material having a diameter larger than 10 mm; the density of the absorbent material in the conformance zone 55 may be substantially uniform; the conformance zone 55 may comprise a substantially homogenous mixture of superabsorbent material and cellulose fibers; the mixture of superabsorbents and cellulosic fibers in the conformance zone may have a basis weight coefficient of variation of at most 20%, as measured according to the method for measuring basis weight evenness provided in this disclosure; the ratio of basis weight of the absorbent material in the conformance zone 55 to the basis weight in the high density areas 60 may be from 1.5 to 4; the ratio of the density of the absorbent material in the conformance zone 55 to the density of the absorbent material in the high density areas 60 may be from 1.5 to 4.

The absorbent components 50 in FIGS. 2A-21 may be used in the absorbent article in FIG. 1 or in any other absorbent article as disclosed herein.

Figure 2A:
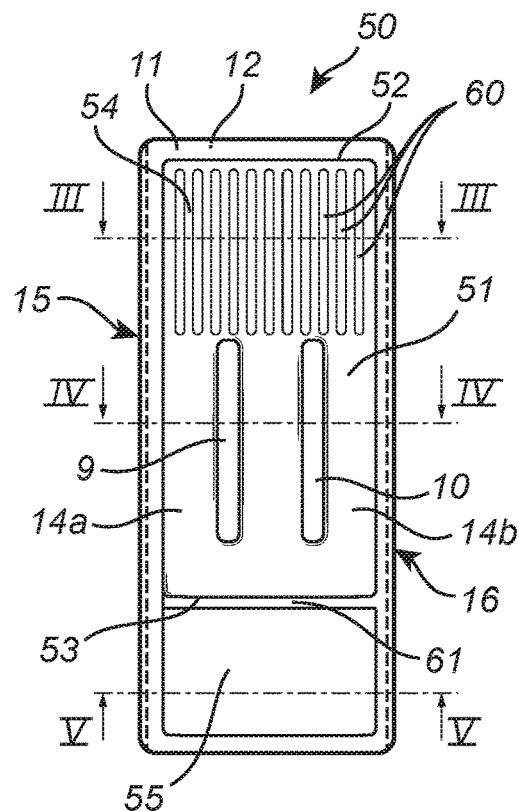
FIGS. 2A-2G show different core configurations.

With reference to FIG. 2A, the coherent area 51 of the absorbent component 50 is a layer of absorbent material having oblong high density areas 60 arranged therein. The oblong high density areas 60 extend in the front portion of the coherent area 51, generally from the front edge 52 of the coherent area 51 to the front ends of two sealed channels 9, 10 which are arranged in the coherent area 51, as disclosed herein.

The oblong high density areas 60 may have a density gradient, with increasing density in a direction from the front edge 52 to the ends of the oblong high density areas 60 in the mid-section of the coherent area 51.

The sealed channels 9, 10 may optionally be supplemented by side seals as disclosed herein. The conformance zone 55 has a rectangular shape and the coherent area (51) and the conformance zone (55) are separated vertically by an area (61) substantially free from absorbent material. The area substantially free from absorbent material may have a basis weight of less than 50 gsm, such as less than 25 gsm, such as less than 5 gsm and may have a width of 2-30 mm, 2-20 mm such as 5-10 mm.

Figure 3:
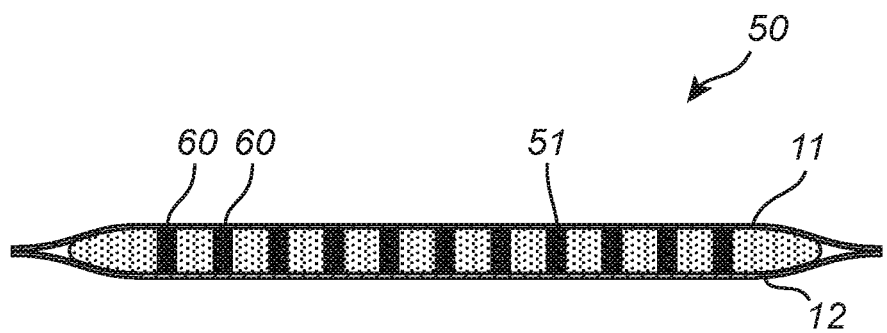
FIG. 3 shows a cross-section taken along the line Ill-Ill in FIG. 2C.

FIG. 3 shows a cross-section taken along the line Ill-Ill in the front portion of the absorbent component 50 shown in FIG. 2A. The oblong high density areas 60 are shown as thickened regions of the absorbent component 50. After formation of the absorbent component 50 in a forming mold, the absorbent component 50 will usually be compacted between two compaction rolls.

Figure 4:
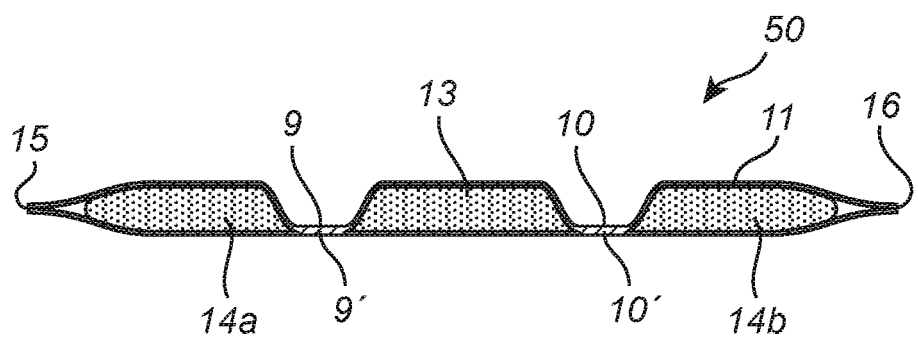
FIG. 4 shows a cross-section taken along the line IV-IV in FIG. 2C.

FIG. 4 shows a cross-section taken along the line IV-IV in the crotch portion of the absorbent component 50 shown in FIG. 2A. The absorbent component 50 which is shown has two longitudinally extending and generally straight sealed channels 9,10 in which the upper core cover side 11 is joined to the lower core cover side 12 by seals 9', 10' extending along the sealed channels 9,10, at the bottom of the sealed channels 9,10. The seals 9', 10' may be provided as bond lines consisting of bonding elements arranged in a bond pattern. A width of each bond line may be less than a width of the corresponding sealed channel 9, 10 in which the bond line is arranged. Thereby, a slack is formed in the core cover material between the edge of the bond line and the edge of the sealed channel in which the bond line is placed. Such slack may be provided to allow expansion room for the absorbent material arranged on either side of the bond lines. The slack may be smaller on the inner side of each sealed channel 9,10 which is facing towards the centre of the absorbent article, and larger on the outer side of each sealed channel 9,10 which is facing towards the side edges of the absorbent article 1.

Furthermore, a central segment 13 is defined in the absorbent component 50 between the sealed channels 9, 10. Two side segments 14a, 14b are defined in the absorbent component 50 outside each sealed channel 9, 10, between the sealed channel 9,10 and a corresponding side seam 15, 16. Accordingly, the first side segment 14a is positioned between the first sealed channel 9 and a first side seam 15, whereas the second side segment 14b is positioned between the second sealed channel 10 and a second side seam 16. The side seams 15, 16 are configured for joining the upper core cover side 11 to the lower core cover side 12, suitably by means of ultrasonic welding, heat sealing, or the like.

As shown in FIG. 4, the absorbent component 50 is divided into a central segment 13 located between the sealed channels 9,10 and two side segments 14a, 14b on either side of the central segment 13.

Figure 5:
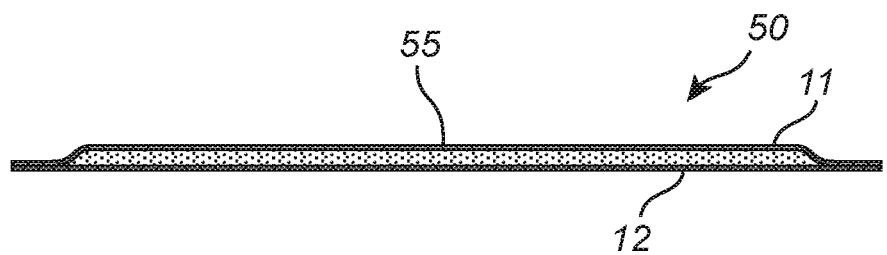
FIG. 5 shows a cross-section taken along the line V-V in FIG. 2C.

FIG. 5 shows a cross-section taken through the conformance zone 55 along the line V-V in FIG. 2A. The absorbent material in the conformance zone 55 may have a lower density than the absorbent material in the high density areas 60 in the coherent area 51. The conformance zone may have, but not necessarily, a lower thickness than the coherent area 51.

Figure 2B:
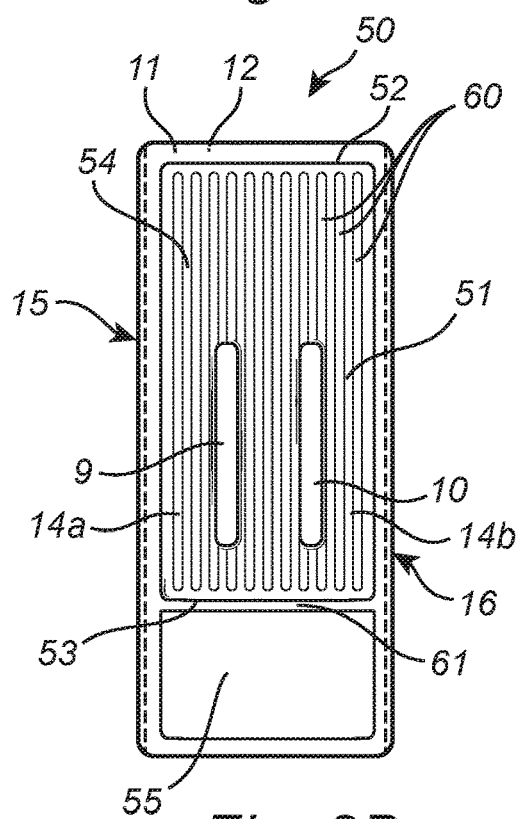

With reference to FIG. 2B, the coherent area 51 of the absorbent component 50 is a layer of absorbent material having oblong high density areas 60 arranged therein. The oblong high density areas 60 extend generally all the way from the front edge 52 of the coherent area 51 to the back edge 53 of the coherent area 51. The oblong high density areas 60 may have a density gradient in the front portion and/or in the back portion of the coherent area 51. The oblong high density areas 60 may have a density gradient extending from the front edge 52 of the coherent area 51 and/or from the back edge 53 of the coherent area 51.

The density of the absorbent material in the oblong high density areas 60 may increase in a direction from the front edge 52 of the coherent area 51 to a mid-section of the coherent area 51 and/or in a direction from the back edge 53 of the coherent area 51 to a mid-section of the coherent area 51 such that the absorbent material in the oblong high density areas is less dense at the front edge 52 of the coherent area 51 and or at the back edge 53 of the coherent area 51 than at the mid-section of the coherent area 51.

The density in the oblong high density areas 60 may increase from the front edge 52 of the coherent area 51 to a transverse centre line through the coherent area 51 and then decrease from the transverse centre line to the back edge 53 of the coherent area.

Further options are:

- That the density in the oblong high density areas 60 increases from the front edge 52 of the coherent area 51 to a transverse line through a forward part of the coherent area 51 and then decreases from the transverse line to the back edge 53 of the coherent area.
- That the density in the oblong high density areas 60 increases from the front edge 52 of the coherent area 51 to a transverse line through a rear part of the coherent area 51 and then decreases from the transverse line to the back edge 53 of the coherent area.
- That the density in the oblong high density areas 60 increases from the front edge 52 of the coherent area 51 to a density gradient free portion of the oblong high density areas 60 arranged in the mid-section of the coherent area 51 and then decreases from the density gradient free portion of the oblong high density areas 60 to the back edge 53 of the coherent area.

The density may increase in the oblong high density areas 60 from the front edge 52 of the coherent area to the mid-section of the coherent area 51 with from 10 kg/m$^3$ to 125 kg/m$^3$.

The density may increase in the oblong high density areas 60 from the front edge 52 of the coherent area to the mid-section of the coherent area 51 with 1 kg/m$^3$ to 5 kg/m$^3$ for each 10 mm.

The density may increase in the oblong high density areas 60 from the back edge 53 of the coherent area to the mid-section of the coherent area 51 with from 10 kg/m$^3$ to 125 kg/m$^3$.

The density may increase in the oblong high density areas 60 from the back edge 53 of the coherent area to the mid-section of the coherent area 51 with 1 kg/m$^3$ to 5 kg/m$^3$ for each 10 mm.

Two sealed channels 9, 10 are arranged in the coherent area 51, as disclosed herein. The sealed channels 9, 10 may optionally be supplemented by side seals as disclosed herein. The conformance zone 55 is rectangular and comprises absorbent material and may not comprise areas free from absorbent material. The absorbent material in the conformance zone 55 may have a lower density than the absorbent material in the high density areas 60 in the coherent area 51. The coherent area 51 and the conformance zone 55 are separated vertically by an area 61 substantially free from absorbent material. The area substantially free from absorbent material may have a basis weight of less than 50 gsm, such as less than 25 gsm, such as less than 5 gsm and may have a width of 2-30 mm, 2-20 mm such as 5-10 mm.

Figure 2C:
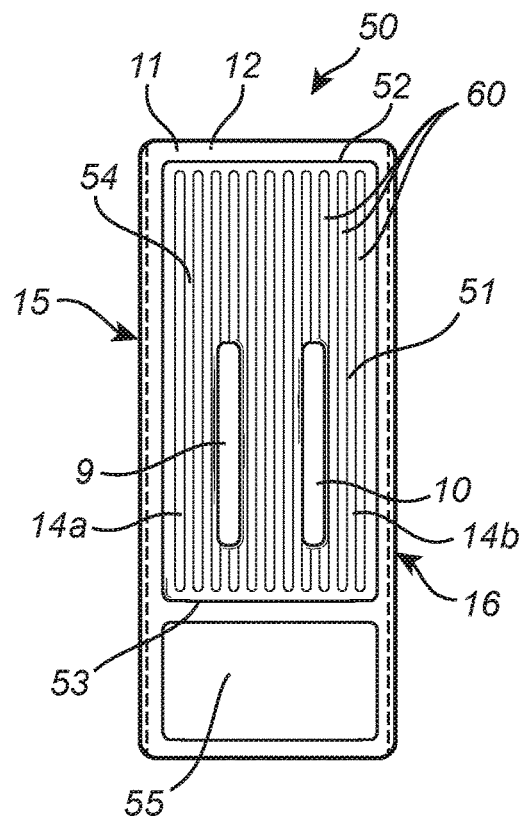

With reference to FIG. 2C, the coherent area 51 of the absorbent component 50 is a layer of absorbent material having oblong high density areas 60 arranged therein. The oblong high density areas 60 extend generally all the way from the front edge 52 of the coherent area 51 to the back edge 53 of the coherent area 51. Two sealed channels 9, 10 are arranged in the coherent area 51. The sealed channels 9, 10 may optionally be supplemented by side seals as disclosed herein. The conformance zone 55 is rectangular and comprises absorbent material and may not comprise areas free from absorbent material. The absorbent material in the conformance zone 55 may have a lower density than the absorbent material in the high density areas 60 in the coherent area 51. The coherent area 51 and the conformance zone 55 are separated vertically by an area 61 substantially free from absorbent material. The area substantially free from absorbent material 61 in FIG. 2C is wider than the corresponding area in FIG. 2B. The area substantially free from absorbent material may have a basis weight of less than 50 gsm, such as less than 25 gsm, such as less than 5 gsm and may have a width of 2-30 mm, 2-20 mm such as 5-10 mm.

Figure 2D:
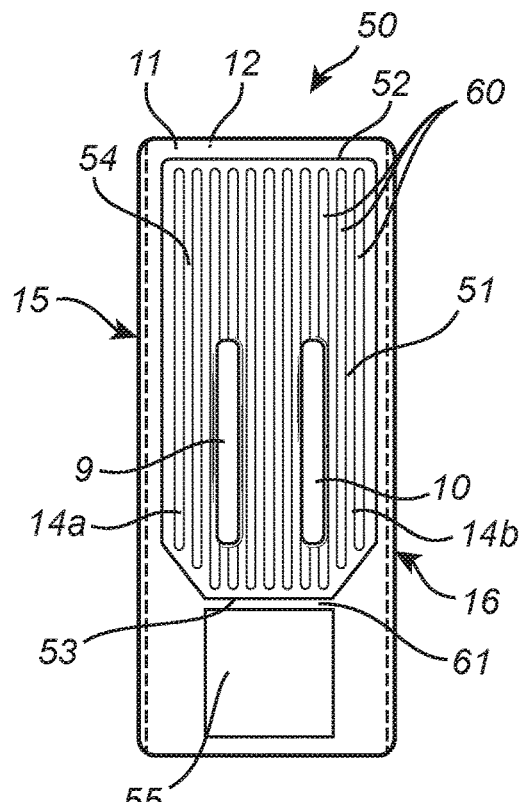

With reference to FIG. 2D, the coherent area 51 of the absorbent component 50 is a layer of absorbent material having oblong high density areas 60 arranged therein. The oblong high density areas 60 extend generally all the way from the front edge 52 of the coherent area 51 to the back edge 53 of the coherent area 51. The high density areas 60 of absorbent material alternate with low density areas 54 of absorbent material. The width of the coherent area 51 decreases in a direction towards the back edge 53 of the coherent area 51. Two sealed channels 9, 10 are arranged in the coherent area 51. The sealed channels 9, 10 may optionally be supplemented by side seals as disclosed herein. The conformance zone 55 has a square shape and comprises absorbent material and may not comprise areas free from absorbent material. The absorbent material in the conformance zone 55 may have a lower density than the absorbent material in the high density areas 60 in the coherent area 51. The coherent area 51 and the conformance zone 55 are separated vertically by an area 61 substantially free from absorbent material. The area substantially free from absorbent material may have a basis weight of less than 50 gsm, such as less than 25 gsm, such as less than 5 gsm and may have a width of 2-30 mm, 2-20 mm such as 5-10 mm.

Figure 2E:
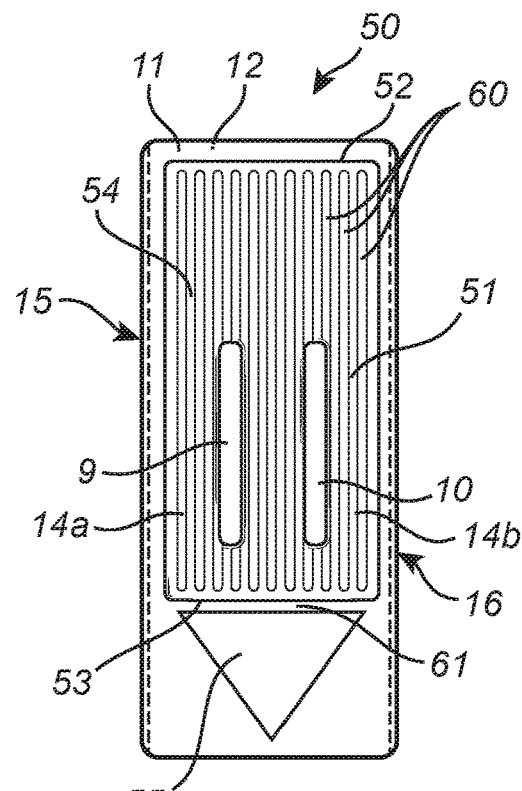

With reference to FIG. 2E, the coherent area 51 of the absorbent component 50 is a layer of absorbent material having oblong high density areas 60 arranged therein. The oblong high density areas 60 extend generally all the way from the front edge 52 of the coherent area 51 to the back edge 53 of the coherent area 51. Two sealed channels 9, 10 are arranged in the coherent area 51. The sealed channels 9, 10 may optionally be supplemented by side seals as disclosed herein. The conformance zone 55 is V-shaped and comprises absorbent material and may not comprise areas free from absorbent material. The absorbent material in the conformance zone 55 may have a lower density than the absorbent material in the high density areas 60 in the coherent area 51. The coherent area 51 and the conformance zone 55 are separated vertically by an area 61 substantially free from absorbent material. The area substantially free from absorbent material may have a basis weight of less than 50 gsm, such as less than 25 gsm, such as less than 5 gsm and may have a width of 2-30 mm, 2-20 mm such as 5-10 mm.

Figure 2F:
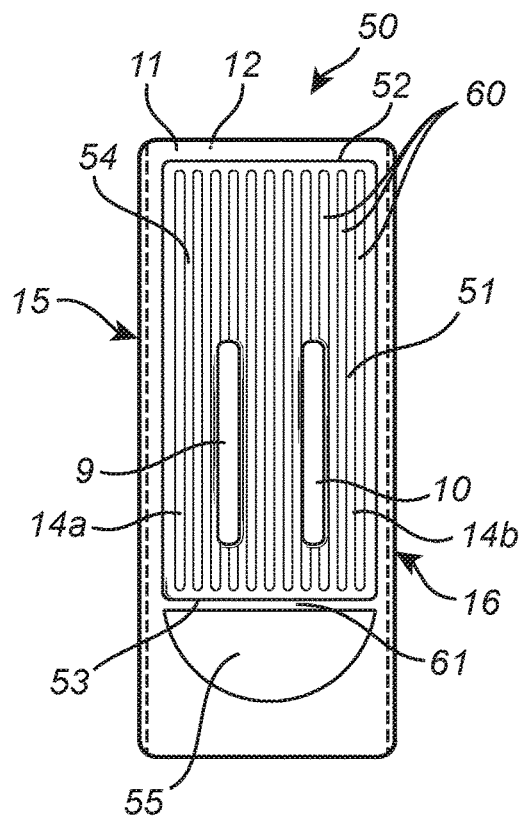

With reference to FIG. 2F, the coherent area 51 of the absorbent component 50 is a layer of absorbent material having oblong high density areas 60 arranged therein. The oblong high density areas 60 extend generally all the way from the front edge 52 of the coherent area 51 to the back edge 53 of the coherent area 51. Two sealed channels 9, 10 are arranged in the coherent area 51. The sealed channels 9, 10 may optionally be supplemented by side seals as disclosed herein. The conformance zone 55 is C- or D-shaped and comprises absorbent material and may not comprise areas free from absorbent material. The absorbent material in the conformance zone 55 may have a lower density than the absorbent material in the high density areas 60 in the coherent area 51. The coherent area 51 and the conformance zone 55 are separated vertically by an area 61 substantially free from absorbent material. The area substantially free from absorbent material may have a basis weight of less than 50 gsm, such as less than 25 gsm, such as less than 5 gsm and may have a width of 2-30 mm, 2-20 mm such as 5-10 mm.

Figure 2G:
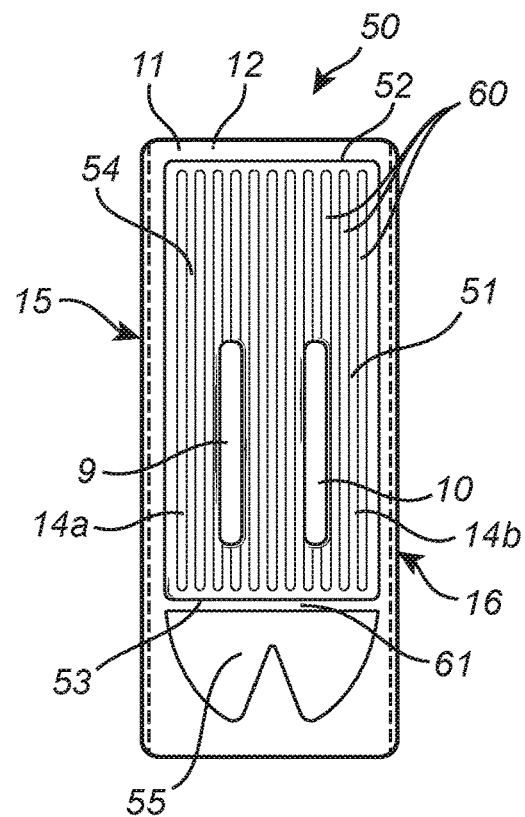

With reference to FIG. 2G, the coherent area 51 of the absorbent component 50 is a layer of absorbent material having oblong high density areas 60 arranged therein. The oblong high density areas 60 extend generally all the way from the front edge 52 of the coherent area 51 to the back edge 53 of the coherent area 51. Two sealed channels 9, 10 are arranged in the coherent area 51. The sealed channels 9, 10 may optionally be supplemented by side seals as disclosed herein. The conformance zone 55 is W-shaped and comprises absorbent material and it does not comprise areas free from absorbent material. The absorbent material in the conformance zone 55 may have a lower density than the absorbent material in the high density areas 60 in the coherent area 51. The coherent area 51 and the conformance zone 55 are separated vertically by an area 61 substantially free from absorbent material. The area substantially free from absorbent material may have a basis weight of less than 50 gsm, such as less than 25 gsm, such as less than 5 gsm and may have a width of 2-30 mm, 2-20 mm such as 5-10 mm.

As disclosed herein, the absorbent article 1 may be provided with components such as elastic barrier cuffs, elastic side panels, skin care agents, odour control material and other components which are commonly used in absorbent articles such as for example baby diapers or incontinence garments. Such additional components are well known in the art and are not described in further detail here.

The disclosure may be varied within the scope of the appended claims. For example, the materials and dimensions used for the different layers forming the absorbent article 1 may be varied, as indicated above. The absorbent article may further include standing gathers, side panels, fastening systems etc. as known sealed channels 9, 10 in the art and depending of the type of absorbent article intended.

EXAMPLES

Methods for Measuring Thickness, Basis Weight and Density

The absorbent core (including the cover sheets) is carefully separated from the other diaper components. The core is then placed flat for 24 hours in a laboratory environment conditioned to 23° C. and 50% relative humidity. Samples from the area of interest are then cut or punched from the core (including the cover sheets). Thickness is measured under a pressure of 0.5 kPa. The thickness gauge foot should rest over the sample for about 5 seconds before reading the thickness value. The sample is then weighed to the nearest milligram. The area of the sample can be determined with a ruler. In case the sample contours are irregular, the sample can be photocopied or scanned, and the area can be determined with a planimeter or suitable image analysis software.

The basis weight ($g/m^2$) is then obtained by dividing the sample weight by the sample area. The density ($kg/m^3$) is obtained according to the formula sample weight/(sample thickness×sample area).

In case individual samples from the area of interest (e.g. ridges or clusters) vary with regards to thickness, basis weight or density, a large number of samples are measured to obtain a representative mean.

Method for Measuring Basis Weight Evenness

For the evaluation, take five adjacent diapers from one and the same consumer package, or take five consecutively produced diapers from production.

Unfold the diapers if folded, and lay bare for 48 hours in a stable laboratory environment set to 23° C. and 50% relative humidity. Testing is performed in this same environment. Remove or neutralize all elastic elements in the diaper and place the diaper smooth and flat. Samples for evenness evaluation are then punched out from the diaper. The punching tool has outer dimensions of 50×120 mm, with cutting cross bars every 20 mm. The tool thus cuts 6 adjacent samples, each sample measuring 50×20 mm (10 cm$^2$). Two sets of 6 individual samples (12 samples in all) are cut from each diaper. Referring to FIG. 3, one set of six samples is taken from the front region (Rf), and the other from the back region (Rb). The punching tool should be placed immediately outside the central region (Rc). The tool's length dimension coincides with the diaper's transverse direction. The punching tool should be centered on the diaper's longitudinal centerline (C).

Determine the weight (to the nearest milligram) of each 50×20 mm core sample. For this purpose, any additional layers (such as the topsheet or the backsheet) first must be subtracted. Take care so that no superabsorbent or significant amounts of fibers are lost when laying bare the core. Alternatively, the punched sample can be weighed as is. The basis weight of the additional layers then must be known beforehand (from the material specification or a separate determination), so that their weight can be subtracted from the samples. Calculate the basis weight (g/m$^2$) for each sample from the large core:

(Sample weight(g))/(Sample area(0.001 m$^2$))

Calculate the (arithmetic) mean basis weight (g/m$^2$) for the series of 60 samples, and then calculate the standard deviation for the series:

Image available on "Original document"

where x is the basis weight of the individual sample, x is the arithmetic mean, and N is the number of samples (count 60).

Finally calculate the coefficient of variation (CV) by dividing the standard deviation by the mean. Express the ratio in percent (%).

The invention claimed is:

1. An absorbent article comprising an absorbent core sandwiched between a liquid-permeable topsheet and a liquid-impermeable backsheet, the article having a longitudinal direction along a central longitudinal axis and a transverse direction along a central transverse axis extending perpendicular to the longitudinal axis, the absorbent article having a front end edge extending in the transverse direction and a back end edge extending in the transverse direction and a first side edge extending in the longitudinal direction and a second side edge extending in the longitudinal direction, the absorbent article comprising a front portion, a back portion and a crotch portion located between the front portion and the back portion, wherein the absorbent core comprises an absorbent component, the absorbent component being enclosed by a core cover, the absorbent component comprising a coherent area, the coherent area having an extension in the longitudinal direction in at least the front portion and the crotch portion of the absorbent article and having an extension in the transverse direction over a full width of the absorbent component inside the core cover, the coherent area having a front edge and a back edge, wherein the absorbent component comprises high density areas of absorbent material alternating with low density areas of absorbent material, the high density areas of absorbent material and the low density areas of absorbent material extending in the longitudinal direction of the absorbent article, in the front portion or in the crotch portion of the absorbent article, wherein the back portion of the absorbent article comprises a conformance zone, and wherein the coherent area and the conformance zone are separated by an area substantially free from absorbent material.

2. The absorbent article according to claim 1, wherein the area separating the coherent area and the conformance zone traverses the whole width of the absorbent component.

3. The absorbent article according to claim 1, wherein the area vertically separating the coherent area and the conformance zone has a basis weight of less than 50 gsm.

4. The absorbent article according to claim 1, wherein the area substantially free from absorbent material has a width of 2-30 mm.

5. The absorbent article according to claim 1, wherein the conformance zone does not comprise areas being free from absorbent material.

6. The absorbent article according to claim 1, wherein the absorbent material in the conformance zone does not comprise individual clusters of absorbent material having a diameter larger than 10 mm.

7. The absorbent article according to claim 1, wherein the absorbent material in the conformance zone has a substantially uniform distribution of the absorbent material.

8. The absorbent article according to claim 1, wherein the density of the absorbent material in the conformance zone is substantially uniform.

9. The absorbent article according to claim 1, wherein the conformance zone comprises a substantially homogenous mixture of superabsorbent material and cellulose fibers.

10. The absorbent article according to claim 1, wherein the mixture of superabsorbents and cellulosic fibers in the conformance zone has a basis weight coefficient of variation of at most 20%, as measured according to the method for measuring basis weight evenness provided in this disclosure.

11. The absorbent article according to claim 1, wherein the conformance zone is symmetrically orientated in relation to the longitudinal axis and wherein the conformance zone has a triangular shape, a D shape, a W shape, a square or a rectangular shape.

12. The absorbent article according to claim 1, wherein the absorbent material in the conformance zone has a lower density than the absorbent material in the high density areas in the coherent area.

13. The absorbent article according to claim 1, wherein the absorbent material in the conformance zone has a lower basis weight than the absorbent material in the high density areas in the coherent area.

14. The absorbent article according to claim 1, wherein the ratio of basis weight of the absorbent material in the conformance zone to the basis weight in the high density areas is from 1.5 to 4.

15. The absorbent article according to claim 1, wherein the ratio of the density of the absorbent material in the conformance zone to the density of the absorbent material in the high density areas is from 1.5 to 4.

16. The absorbent article according to claim 1, wherein the high density areas are oblong areas.

17. The absorbent article according to claim 16, wherein the oblong high density areas have a width of from 3 mm to 30 mm.

18. The absorbent article according to claim 16, wherein the oblong high density areas have a length to width ratio of from 2 to 135.

19. The absorbent article according to claim 15, wherein the absorbent component comprises 3 to 20 oblong high density areas of absorbent material alternating with oblong low density areas of absorbent material, the oblong high density areas of absorbent material and the oblong low density areas of absorbent material extending in the longitudinal direction of the absorbent article, in the front portion or in the crotch portion of the absorbent article.

20. The absorbent article according to claim 1, wherein the coherent area comprises at least one area which is substantially free from absorbent material.

21. The absorbent article according to claim 1, wherein the density of the absorbent material in the low density areas is 50 kg/m3 or less.

22. The absorbent article according to claim 1, wherein the density of the absorbent material in the high density areas is from 130 kg/m3 to 300 kg/m3.

23. The absorbent article according to claim 1, wherein the core cover has an upper side and a lower side, the absorbent component comprising a sealing arrangement joining the upper and lower sides of the core cover, the sealing arrangement comprising at least one sealed channel extending in the longitudinal direction of the absorbent article, the sealed channel being free or substantially free from absorbent material.

24. The absorbent article according to claim 1, wherein the high density areas of absorbent material and the low density areas of absorbent material extend in the longitudinal direction of the absorbent article in the front portion and in the crotch portion of the absorbent article.

* * * * *